United States Patent [19]
Genis

[11] Patent Number: 5,257,429
[45] Date of Patent: Nov. 2, 1993

[54] THERAPEUTIC HEAD AND NECK REST

[76] Inventor: Mark Genis, 2439 Horseshoe Canyon Rd., Los Angeles, Calif. 90046

[21] Appl. No.: 24,337
[22] Filed: Mar. 1, 1993
[51] Int. Cl.⁵ .............................................. A47G 9/00
[52] U.S. Cl. .......................................... 5/636; 5/640; 5/644; 607/109; 607/114
[58] Field of Search ................. 5/421, 636, 640, 644, 5/645; 128/376, 403

[56] References Cited

U.S. PATENT DOCUMENTS

| | | | |
|---|---|---|---|
| 2,783,807 | 3/1957 | Duffield | 128/403 X |
| 3,900,910 | 8/1925 | Nakata | 5/636 X |
| 3,911,512 | 10/1925 | Plate | 5/636 |
| 4,071,031 | 1/1978 | Lowman | 5/421 X |
| 4,236,264 | 12/1980 | Britzman | 5/640 |
| 4,783,866 | 11/1988 | Simmons et al. | 5/644 X |
| 4,887,326 | 12/1989 | O'Brien et al. | 5/644 X |

Primary Examiner—Michael F. Trettel

[57] ABSTRACT

A therapeutic rest is disclosed herein having a first pillow composed of a soft tufted cover filled with a cushion material and a second pillow composed of a soft flexible material intended to be filled with a liquid of suitable temperature. A removable valve is incorporated into the second pillow for introducing the liquid into and out of the second pillow. The first and second pillows are of a U-shaped configuration and releasable retainers are carried on opposing exterior surfaces of the pillows to permit attachment of the pillows when the pillows are in aligned U-shaped configuration.

9 Claims, 1 Drawing Sheet

THERAPEUTIC HEAD AND NECK REST

BACKGROUND OF THE INVENTION

1. Field of the Invention

The present invention relates to the field of therapeutic devices, and more particularly to a novel combination of a first and second pillow that are detachably connected together via their opposing external surfaces wherein a first pillow contains cushion material while the second pillow contains a liquid of desired temperature.

2. Brief Description of the Prior Art

In the past, it has been the conventional practice to provide a therapeutic pillow for use about the neck and beneath the head of the user which combines a fiber cushion material within a covering and wherein the covering includes a pouch or pocket into which a frozen gel pack may be inserted in order to provide a therapeutic relief for the user. Such a therapeutic pillow is disclosed in U.S. Pat. No. 4,858,259. Problems and difficulties have been encountered when employing such a conventional pillow, which stem largely from the fact that the gel pack must be refrigerated prior to being inserted into the pocket or pouch of the covering. Also, the covering must be constructed to accommodate not only the fiber cushion material but the special pouch and which further includes a flap or closure of some nature for retaining the refrigerated pack in place once it has been inserted.

Such a conventional device is expensive to manufacture and requires the user to have special knowledge as to preparation of the gel pack, storage of the gel pack and insertion of the gel pack preparatory for use in the special cover. Furthermore, such a conventional therapeutic pillow does not accommodate the user by using a temperate or heated liquid which would provide therapeutic relief. The prior pillow is limited to a refrigerated pack which is inserted into the pouch. The refrigerated pack is self-contained and includes no means for removing the gel within the pack and replacing it with other liquids of differing temperature than cold or cool.

Therefore, a long-standing need has existed to provide a therapeutic pillow arrangement which not only includes the fiber cushion but incorporates a separate pillow having a closure means which permits liquids of different temperatures to be introduced into the second pillow or removed therefrom. Furthermore, means are required for detachably connecting the first pillow to the second pillow so that the head of the user is comforted while the therapeutic effect of the hot or cold liquid in the second pillow provides therapeutic effect to neck and shoulder areas.

SUMMARY OF THE INVENTION

Accordingly, the above problems and difficulties are overcome by the present invention which provides a combination of a first pillow and a second pillow which are detachably connected together via external retainers whereby the user's head rests against the first pillow and the user's neck and shoulder engage with the second pillow. In one form of the invention, the first pillow includes a fibrous cushion material within a cover having a tufted surface adapted to be engaged by the user's head and a second pillow beneath the first pillow which contains a fluid of a desired temperature. The closure means is removable and carried on the second pillow so that the liquid may be readily introduced into the second pillow or removed therefrom at the will of the user. No special preparation of the liquid or the second pillow is needed. Means are incorporated into the retaining means for removably connecting the pillows together so that a watertight securement is achieved on the second pillow to prevent leakage of the contained liquid.

Therefore, it is among the primary objects of the present invention to provide a novel therapeutic pillow which comprises a fiber cushion and a separate and individual second pillow containing a therapeutic liquid and means for interconnecting the two pillows via their external surfaces whereby the first pillow cushions the user's head and the second pillow applies the benefits of the therapeutic liquid into the neck and shoulders thereof.

Another object of the present invention is to provide a novel therapeutic pillow which is simple to manufacture and to assemble by the user so that both the head and shoulders of the user are comforted and the effects and benefits of a therapeutic liquid carried in the second pillow are applied to the user's neck and shoulder area.

Still a further object of the present invention is to provide a novel therapeutic rest for the user's head which includes a separate and individual pillow containing a therapeutic fluid which applies the benefits directly to the neck and shoulder area of the user.

Still a further object of the present invention is to provide a novel first and second pillow combination which are releasably joined together via external fasteners or retainers and which permits the second pillow to adjust to the contour of the user's neck and shoulders.

A further object of the invention resides in a therapeutic pillow combination whereby first and second pillows may be used separately or together in order to provide benefit to the user in a comfortable manner for supporting the head, neck and shoulders.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DESCRIPTION OF THE PREFERRED EMBODIMENT

Figure 1:
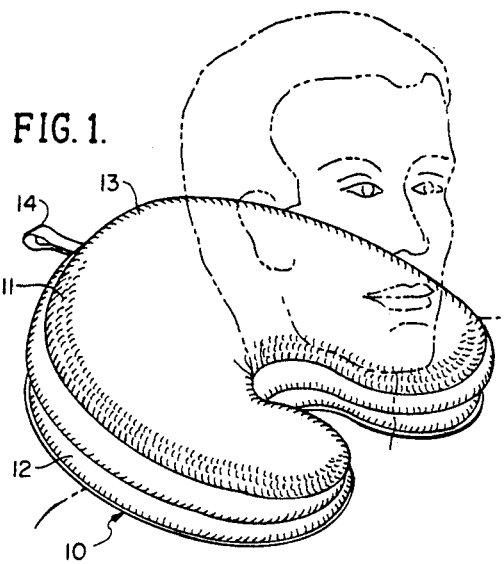
FIG. 1 is a front perspective view of the novel therapeutic pillow of the present invention.

Referring to FIG. 1, the novel therapeutic pillow combination of the present invention is illustrated in the direction of arrow 10, which includes a first pillow 11 that is detachably connected to a second pillow identified by numeral 12. The pillow 11 and the pillow 12 are of U-shaped configuration and are placed in alignment so that their peripheral edges will coincide so as to leave a space adapted to accommodate the neck of the user, as illustrated in broken lines. The pillow 11 is substantially composed of a fabric covering having a tufted surface 13 and which is filled with a suitable cushion material such as a foam or other soft material. The cover for pillow 11 does not provide an entrance and the interior is stuffed with the cushion material only. A convenience loop 14 is stitched to the back of cushion 11 and is used for storage and handling purposes.

With respect to the second pillow 12, it is to be noted that the pillow is composed of a plastic-like material so as to hold a temperature retaining substance such as ice, water or the like.

Figure 2:
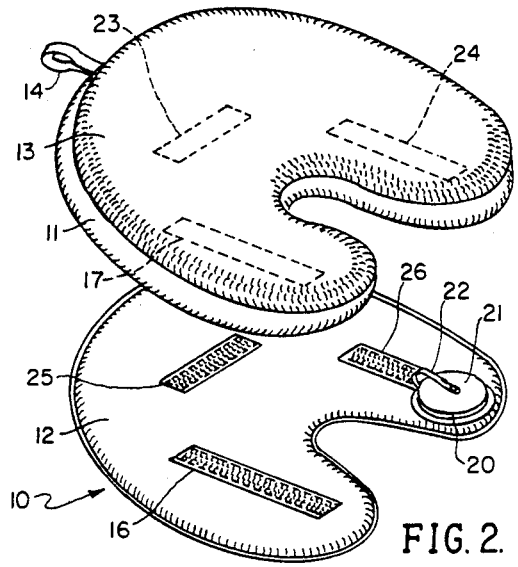
FIG. 2 is an exploded view of the pillow shown in FIG. 1 illustrating the separate and individual pillows comprising the cushion shown in FIG. 1.

Referring now in detail to FIG. 2, an exploded view illustrates that the pillow combination 10 includes the cushion pillow 11 and the temperature retaining material filled pillow 12 in detachable relationship. It can be seen that pillow 12 includes an exterior surface on which one-half of a closure means is provided, while the underside of pillow 11 includes the other half of the fastener or closure means. In the present instance, the closure means may take the form of a conventional hook-and-pile fastener wherein the hook portion is indicated by numeral 16 and the pile component of the closure is indicated by numeral 17. It is noted that the fastener or closure means are placed in registry so that when the opposing exterior surfaces of the cushion pillow and the temperature retaining material pillow 12 are aligned and pressed together, a unitary construction ensues. The peripheral edges of the two pillows are in alignment and registry so that the space for accommodating the user's neck is well defined. In one form, the second pillow 12 is composed of a pair of plastic-like material sheets which are heat-sealed together along their outer peripheral edge so as to form a bladder that is hollow on the inside and adapted to store the temperature-retaining material, such as ice, hot water, cold water or the like. In order to place the temperature-retaining material into the second pillow or bladder 12, an inlet 20 is provided which has a covering cap 21 adapted to be removed when it is desired to open the inlet and close in order to close the inlet. A tethering strap 22 is employed for tethering the cap 21 to the outlet 20 so that the cap will not be lost when the cap has been removed from the outlet.

Figure 3:
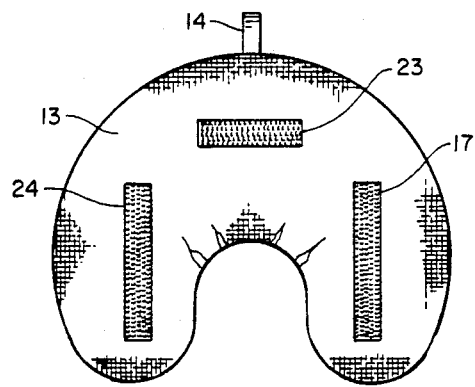
FIG. 3 is a bottom view of the first pillow of the combination illustrating attachment or releasable retaining means.
Figure 4:
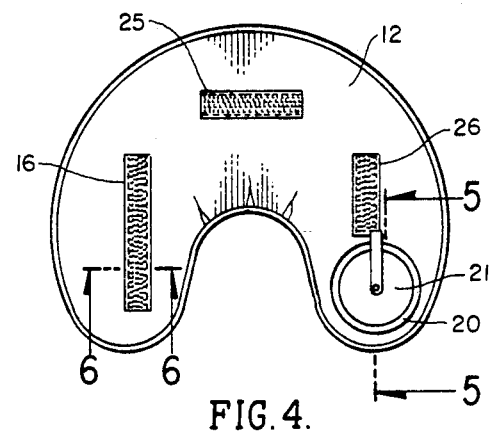
FIG. 4 is a bottom view of the second pillow shown in FIG. 2 illustrating the closure means intended to close with the attachment means shown in the view of FIG. 3.

As shown in FIG. 3, the first pillow 13 is preferably composed of a fabric cover having a cushion material inside and the underside of the pillow mounts the closure means taking the form of the hook-and-pile closure constituting strips 17, 23 and 24. The closure strips are located in fixed spaced-apart relationship and are intended to mate with their opposite closing strips 16, 25 and 26 associated with the second pillow or bladder 12. Therefore, it can be seen that when the first and second pillows are aligned so that the respective closure strips of the closure means are in registry, the two pillows will be attached to one another so that the peripheral edges are aligned and mated. The cap and outlet is sandwiched between the opposing surfaces of the pillows when attachment is complete.

Figure 5:
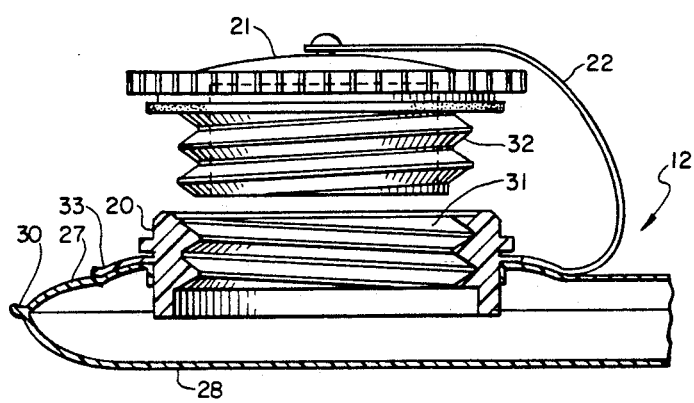
FIG. 5 is an enlarged transverse cross-sectional view of the capped inlet for introducing fluid into the second pillow.

Referring now to FIG. 5, it can be seen that the second pillow 12 comprises sheets 27 and 28 which are joined together about their edge marginal regions such as by heat-sealing along seam 30. Also, it can be seen that the outlet 20 comprises a collar having internal threads 31 adapted to be threadably connected with the external threads 32 of the cap 21. The collar 20 is attached to sheet 27 by means of a heat-sealed flap 33 to the sheet 27.

Figure 6:
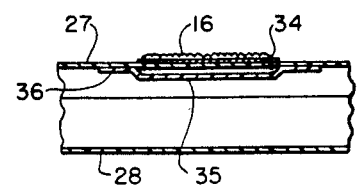
FIG. 6 is an enlarged transverse cross-sectional view of the attachment means for the retainer strips as shown in FIG. 4 as taken in the direction of arrows 6—6 thereof.

Referring now in detail to FIG. 6, it can be seen that the closure strip 16 is stitched to the upper sheet 27 by means of threaded stitches 34. In order to provide a waterproof seal, an elongated plastic strip 35 is placed against the inner surface of the sheet 27 during manufacture so as to cover the stitching which protrudes through the sheet. The surrounding and peripheral edges of the strip 16 are heat-sealed to provide waterproof sealing and the heat seal is indicated by numeral 36.

When it is desired to use the therapeutic device 10 of the present invention, either ice in a solid form, cold water or hot water as a medium can be introduced into the bladder, bag or pillow 12 through the opening of the inlet 20 when the cap is removed. The cap 21 can readily be removed to permit opening of the inlet in order to accommodate the medium passing therethrough. Upon filling, and securement of the cap, the outside of the bladder may be toweled dry so as to remove any of the medium that may have spilled on the outside of the bag or bladder. Preferably, for the user's safety, the temperature of ice water should not fall below 36 degrees F., while hot water should not exceed 100 degrees F. Next, the first cushion pillow 11 is placed in registry with the second pillow 12 so that the closure means will engage and effect securement. The opposing surfaces of the pillows will come into engageable contact and the cap 21 will be wholly or partially covered. The two U-shaped pillows are registered or indexed so that the opening for the user's neck in both pillows will be mated.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A therapeutic device comprising:
   a first cushioned pillow filled with a soft resilient material having a pair of spaced-apart extensions forming a substantially U-shape with said pair of extensions constructed to fit around the back and a portion of the sides of a human neck;
   a second pillow of U-shaped configuration characterized as a flexible plastic container means shaped to mate with said first pillow and being filled with a solution formulated to retain hot or cold temperatures for a substantial period of time; and
   attachment means cooperatively carried on opposing exterior surfaces of said first and second pillows for releasably joining said pillows together to provide a unitary construction.

2. The invention as defined in claim 1 wherein:

said second pillow is a watertight bladder having a pair of sheets joined at their peripheral edges to define said container means;

an inlet port carried on a selected one of said sheets permitting said solution to be passed into and out of said container means; and a removable cap threadably engageable with said inlet to close the interior of said container means from ambient atmosphere.

3. The invention as defined in claim 1 wherein:

a closable inlet port disposed on said second pillow includes a flanged collar having a threaded receptacle for threadably receiving a cap having a threaded shank;

said collar terminating with a raised ridge and said cap having an annular shoulder;

an annular resilient seal carried about said shank separating said shoulder from said ridge; and a strap having opposite ends attached to said cap and said collar respectively.

4. The invention as defined in claim 1 wherein:

said attachment means includes hook-and-pile closure strips carried on opposing surfaces of said first and second pillows for releasably joining said pillows together.

5. The invention as defined in claim 4 wherein:

said strips are sewn onto the exterior surface of said pillows by a plurality of stitches;

a vinyl strip covering said stitches associated with said second pillow having its peripheral edge marginal region heat-sealed directly to said second pillow.

6. A therapeutic device for the neck and shoulders of the user comprising:

a head pillow having a fabric cover enclosing a cushion material;

a shoulders pillow composed of a watertight plastic material storing a solution formulated to retain hot or cold temperatures;

attachment means cooperatively carried on said head pillow and said shoulders pillow for detachably joining said pillows together in a unitary construction;

said attachment means is a hook-and-pile fastener having a hook closure strip of hooks and a pile closure strip of pile.

7. The invention as defined in claim 6 wherein:

said head pillow and said shoulders pillow each have a pair of spaced-apart extensions forming a substantially U-shape;

said attachment means closure strips on said head pillow and said shoulders pillow being aligned to join said pillows in U-shaped registry.

8. The invention as defined in claim 6 including:

a closeable inlet port disposed on said shoulders pillow having a flanged collar and having a threaded receptacle for threadably receiving a cap having a threaded shank;

said collar terminating with a raised ridge and said cap having an annular shoulder; and an annular resilient seal carried about said shank separating said shoulder from said ridge.

9. The invention as defined in claim 8 wherein:

said fastener closure strips carried on opposing surfaces of said pillows;

said hook strips attached to said head pillow and said pile strips attached to said shoulder pillow.

* * * * *